United States Patent [19]

Wong et al.

[11] Patent Number: 5,385,547
[45] Date of Patent: Jan. 31, 1995

[54] ADAPTOR FOR DRUG DELIVERY

[75] Inventors: Joseph Wong, Lake Villa, Ill.; Ray W. Wood, Elkhorn, Wis.; James McShane, Mt. Prospect, Ill.

[73] Assignee: Baxter International Inc., Deerfield, Ill.

[21] Appl. No.: 978,555

[22] Filed: Nov. 19, 1992

[51] Int. Cl.⁶ .............................................. A61M 37/00
[52] U.S. Cl. ........................................ 604/87; 604/414
[58] Field of Search ................................... 604/82–84, 604/86–88, 90, 56, 201, 204, 205, 403, 411, 412, 414–416

[56] References Cited

U.S. PATENT DOCUMENTS

| | | | |
|---|---|---|---|
| 4,392,850 | 7/1983 | Elias et al. | 604/82 |
| 4,432,755 | 2/1984 | Pearson | 604/56 |
| 4,559,983 | 12/1985 | Paoletti | 141/260 |
| 4,589,879 | 5/1986 | Pearson | 604/411 |
| 4,645,073 | 2/1987 | Homan | 206/219 |
| 4,798,605 | 1/1989 | Steiner et al. | 604/411 |
| 4,804,366 | 2/1989 | Zdeb et al. | |
| 4,850,978 | 7/1989 | Dudar et al. | |
| 4,898,209 | 2/1990 | Zbed. | |
| 4,932,937 | 6/1990 | Gustavsson et al. | 604/87 |
| 5,074,844 | 12/1991 | Zdeb et al. | 604/83 |
| 5,167,642 | 12/1992 | Fowles | 604/263 |
| 5,226,900 | 7/1993 | Bancsi et al. | 604/411 |

FOREIGN PATENT DOCUMENTS 8101241 5/1981 WIPO .................... 604/414

OTHER PUBLICATIONS

Abbott Laboratories publication entitled "Add-Vantage; The New Standard for Simplicity and Savings".
Published PCT Application, WO 91/11152, published Aug. 8, 1991.
Baxter Publication entitled "Initiate Your Own Time-Saving Program", May 1992.
Baxter Publication entitled "A New Force Is Coming To Light in IV/Drug Delivery", Jun. 1989.
IVAC Corporation publication entitled "Cris System".

Primary Examiner—C. Fred Rosenbaum
Assistant Examiner—V. Alexander
Attorney, Agent, or Firm—Paul E. Schaafsma; Amy L. H. Rockwell; Paul C. Flattery

[57] ABSTRACT

A drug delivery device is provided for coupling a first container including a beneficial agent to a second member. In an embodiment, the device includes a substantially hollow member having a cannula mounted within a wall that divides the substantially hollow member into a first and second section. The first section includes means for receiving at least a portion of a first container. The substantially hollow member includes a wall that defines an exterior of the first section that is substantially flexible. A number of different cannula and flow path structures within the hollow member are possible pursuant to the present invention.

47 Claims, 3 Drawing Sheets

ADAPTOR FOR DRUG DELIVERY

BACKGROUND OF THE INVENTION

The present invention relates generally to the delivery of a beneficial agent to a patient or into a system for later delivery to a patient. More specifically, the present invention relates to an improved drug delivery system.

For many applications, drugs can be mixed with a diluent before being delivered, for example, intravenously to a patient. The diluent can be, for example, a dextrose solution, a saline solution, or even water. To this end, many drugs are supplied in powdered form and packaged in glass vials. Other drugs, such as some chemotherapy drugs, are packaged in glass vials in a liquid state.

Powdered drugs can be reconstituted by utilizing a syringe to inject liquid into a vial for mixing; the syringe eventually withdrawing the mixed solution from the vial. When a drug must be diluted before delivery to a patient, the drug is often injected into a container of diluent after it is reconstituted; a container can be connected to an administration set for delivery to the patient.

Drugs may be packaged separate from the diluent for various reasons. One of the most important reasons is that many drugs do not retain their chemical and physical stability when mixed with a diluent and thus cannot be stored for any substantial period of time. Also, drugs are often packaged separately from the diluent because many companies that manufacture drugs are not engaged in the business of providing medical fluids and containers for intravenous delivery, and vice versa.

Therefore, doctors, nurses, pharmacists, or other medical personnel must mix the drug and diluent. This presents a number of problems. The reconstitution procedure is time consuming and requires aseptic techniques. The operator must provide the proper diluent and a syringe before beginning. The reconstitution procedure should be performed preferably or under preferably sterile conditions. This requirement requires the operator to be more cautious, thereby consuming more time. Additionally, sterile conditions are often hard to maintain. In some instances, a laminar flow hood may be required under which the reconstitution procedure is performed.

A further concern is that some drugs, such as chemotherapy drugs, are toxic. Exposure of the operator to the drugs during reconstitution can be dangerous, especially if the operator works with such drugs on a daily basis and is repeatedly exposed to them.

Although after a drug is reconstituted and withdrawn into a syringe barrel, the drug can, in some instances, be injected immediately into a patient, more typically, however, the reconstituted drug is injected from the syringe into a larger container of solution for connection to an intravenous administration set. A larger container of solution may be necessary because often the reconstituted drug in the syringe is at such a concentration as to cause local toxicity in the veins of a patient near the injection site where the needle pierces the skin. This can create severe vein irritation which can be harmful.

Additionally, even though the proper dose of medication may be in the syringe, immediate injection into the patient's blood stream can create a condition of systemic toxicity wherein the level of drug concentration in the patient's entire blood system is dangerously high.

Yet another reason for not making an injection from the syringe directly into the patient is that such an injection creates an additional injection site into the patient; this can be painful for the patient and provides another opportunity for infection.

For these reasons, the reconstituted drug is more typically injected into a diluent container.

A number of drug delivery systems are known.

In one delivery system that is currently used, a drug contained in a vial in a solid state is reconstituted with a predetermined volume of diluent using a needle and syringe. The vial containing the drug and solution is then mated onto an intravenous administration set. The drug is delivered to a patient as diluent flows through the vial to the patient carrying with it the dissolved drug.

In another IV drug delivery system, the drug solution is packaged in flexible plastic containers. Some drugs packaged in this manner may be stored at room temperature and the drug is delivered by connecting the container to an intravenous administration set. Some drugs packaged in this manner may be stored in a frozen state in order to improve drug stability. In these cases, the drug solution must be thawed and then connected to an intravenous administration set for delivery to the patient.

Another system requires drugs to be contained in a special vial. An activated vial is then mated to a special container. The vial stopper is removed and the drug is transferred to the container by flushing the vial with the diluent in the container. The drug is delivered by connecting the container with the dissolved drug to an intravenous administration set.

Drugs can also be delivered intravenously via a syringe pump. Briefly, a dose of reconstituted drug solution is withdrawn by a syringe. The drug solution in the syringe is then refrigerated or frozen until use. The drug solution is brought to room temperature and infused into a patient via a syringe pump.

There are some disadvantages with some of the above systems and procedures. One of the disadvantages is drug waste. Due to chemical and physical instability, once a solid drug is reconstituted with diluent (or a frozen formulation is thawed), it cannot be stored for any substantial amount of time. Therefore, if the drug solution is not administered to the patient within a given period of time, the drug must be discarded. Drug waste can be a very costly expense to a hospital pharmacy.

Some of the current procedures for intravenous administration are labor intensive. As previously noted, reconstitution of a drug with a needle and syringe is time consuming and requires an aseptic environment. Likewise, exposure of the operator to the drug may be dangerous, especially if the operator works with the drug on a daily basis. Of course, needle sticks may expose healthcare professionals to hazardous diseases and infections.

A further disadvantage of some of the above procedures is that they require a secondary IV administration set for delivery of the drug. The secondary set can be cumbersome for both the patient and the clinician. Elimination of the secondary set (along with the needle and syringe) may also reduce solid waste and disposal costs.

U.S. Pat. No. 4,850,978 discloses a drug delivery system for delivering drugs to patients and/or reconstitution of a drug. The system includes a cartridge for introducing a beneficial agent into a fluid conduit for delivery of the agent to a patient. The cartridge includes a rigid hollow tube and an agent containing chamber slidably mounted at least partially within the hollow tube. In a first, pre-use position, the chamber extends farther from the hollow tube than it does in a second position. A cannula is mounted to the hollow tube extending opposite the chamber. When the chamber is in the second position, the cannula pierces the closure means creating a flow path.

U.S. Pat. No. 4,804,366 also discloses a drug delivery system including an adapter having an improved flow path means providing both an inlet and an outlet to the agent containing chamber of a cartridge. The cartridge and adapter permit a single opening through the injection sites at opposite ends of the flow path means, while still permitting simultaneous flow both into and out of the chamber. An adapter and a cartridge is provided, including a rigid cannula with an inlet and an outlet and the shell substantially coaxial with and spaced from the cannula intermediate of the cannula inlet and the cannula outlet so that the shell of the cannula defines a channel therebetween. Both the cannula inlet and the cannula outlet are adaptable to form a single piercing opening in a resilient injection site associated with the cartridge.

SUMMARY OF THE INVENTION

The present invention provides an improved drug delivery system. The system facilitates the reconstitution and intravenous administration of a beneficial agent. Generally, pursuant to the present invention, an adaptor is provided that provides a for connection to an in-line IV set, a site for connection to a vial containing a beneficial agent, and the adaptor includes at least an upper section for containing a volume of diluent, the upper section including portions thereof that can be biased inwardly; in a preferred embodiment, the portions that can be biased inwardly are flexible walls. A cannula can be mounted within the adaptor.

To this end, a device is provided for coupling a first container including a beneficial agent to a second member. In an embodiment, the device includes a substantially hollow member having a spike mounted within a wall that divides the substantially hollow member into a first and second section. The second section includes means for receiving at least a portion of a first container. The substantially hollow member includes a wall that defines an exterior of the first section that is substantially flexible. In an embodiment, the hollow member has a tube-like shape.

A number of different cannula and flow path structures within the hollow member are possible pursuant to the present invention. In an embodiment, a shell circumscribes a portion of the cannula and defines a channel having an inlet and an outlet. The shell and cannula can extend for the same distance into the upper section or the shell and cannula can extend at different distances into the upper section. In an embodiment, the device includes two cannulas located therein.

For use with an in-line IV set, the present invention also provides a cartridge for introducing a beneficial agent into a fluid conduit for delivery of the beneficial agent. In an embodiment, the cartridge includes a hollow tube having a cannula mounted therein defining a channel having an inlet and an outlet. A shell circumscribes a portion of the hollow tube and defines a channel also having an inlet and an outlet. The hollow tube includes a wall member dividing the hollow tube into an upper section and lower section, the channels of the cannula and shell passing through the wall. The upper section is so constructed and arranged to receive at least a portion of the vial including a beneficial agent. The upper section is defined, at least in part, by substantially flexible walls.

Preferably, the upper section is divided into a section for housing a diluent and a top portion for receiving a portion of a vial.

Preferably, the hollow member includes means for piercing a closure of the vial when the vial is received by the upper section.

A method of delivering a drug is also provided. The method comprises the steps of: providing an adaptor including an upper section having at least partially flexible walls and a cannula providing fluid communication between the upper section and an outlet of the cannula; providing the upper section with a diluent; coupling a vial of beneficial agent to the upper section and establishing fluid communication between an interior of the vial and the upper section; causing fluid to flow into the vial by, at least in part, squeezing at least a portion of the walls of the upper section; allowing a resultant product to flow from the vial into the upper section; and causing the resultant product to flow through the outlet of the cannula.

Due to the flexible walls that define the first section, diluent can be easily added to the vial. This allows the drug contained within the vial to be reconstituted and/or mixed with the diluent in the vial. The resultant product can then be transferred back to the adaptor.

By utilizing different constructions of the adaptor, including the cannula and shell arrangement located therein, drug delivery profiles can be modified. This allows a variety of drugs to be delivered utilizing the adaptor.

An advantage of the present invention is that it provides an adaptor that allows an in-line IV set to be used with any off-the-shelf drug vial.

A further advantage of the present invention is that it could shorten product developmental times since all drugs contained in their respective manufacturer's vials have established expiration.

Moreover, an advantage of the present invention is that it reduces pharmacist's time and the additional expenses with respect to the use of needles and syringes.

And further, an advantage of the present invention is that the adaptor is user friendly, for example, a nurse can activate and reconstitute the drug in a single step.

Still further, an advantage of the present invention is that it reduces waste, the activation/reconstitution procedure can be done immediately prior to administration.

An advantage of the present invention is that it does not require a specially designed vial and accordingly, it eliminates the cost for putting drugs into specially designed vials.

Additionally, an advantage of the present invention is that it reduces waste in contrast to some systems wherein once the specially designed vial is placed into an on-line IV system, it must be used; because the adaptor of the present invention is not activated until immediately prior to administration, this greatly reduces the potential for drug waste.

Furthermore, an advantage of the present invention is that a piggy back is not required.

Another advantage of the present invention is that the adaptor can allow the delivery of drugs in volumes as low as a bolus injection with a syringe or in volumes and concentrations similar to intravenous drip infusion.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides adaptors for coupling a vial containing a beneficial agent to an in-line IV set. Additionally, the present invention provides improved methods for administering a drug to a patient. As set forth in detail hereinafter, due to the construction of the adaptor of the present invention, it can be utilized with most any intravenous drug. To this end, the adaptor can be modified to provide drug delivery profiles allowing the administration of many varied drugs.

Figures 1, 2, 3:
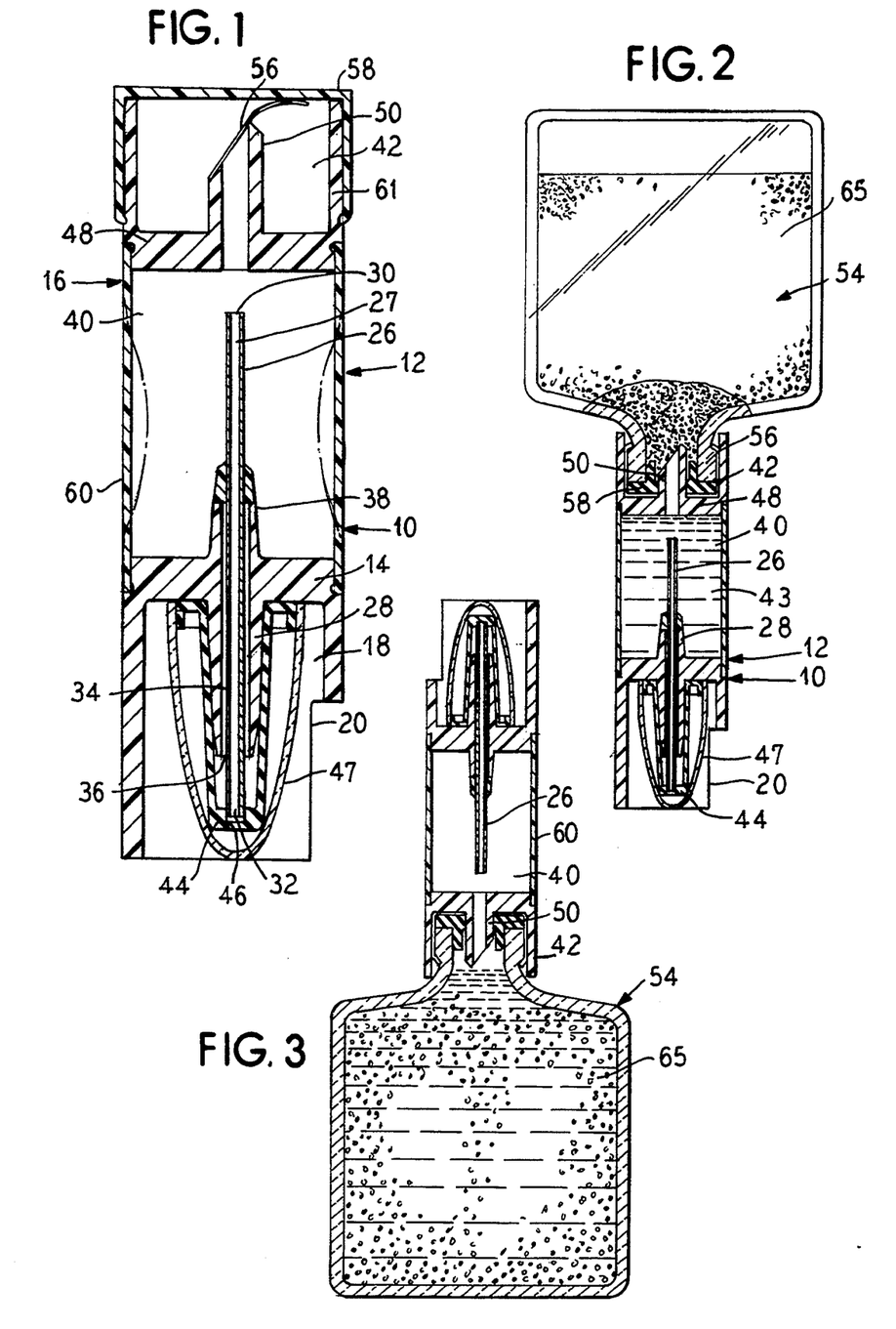
FIG. 1 illustrates a cross-sectional view of an embodiment of the adaptor of the present invention.
FIG. 2 illustrates an embodiment of the adaptor of the present invention wherein a vial has been mated to the adaptor.
FIG. 3 illustrates a cross-sectional view of the adaptor and vial arrangement of FIG. 2 wherein diluent from the adaptor has been added to the vial.

Referring now to FIG. 1, an embodiment of the adaptor 10 is illustrated. As illustrated, the adaptor 10 preferably comprises a substantially tubular-shaped cartridge 12 that is divided by a wall 14 into an upper section 16 and a lower section 18. The lower section comprises a substantially rigid member having a key wall 20. The wall 14 is mounted across the cartridge 12 and defines the starting point for the key wall 20.

In the preferred embodiment illustrated, a cannula 26 extends through the wall 14. The cannula 26 defines a channel 27. Additionally, a generally cylindrical shell 28 extends from both sides of the wall 14.

The shell 28 is spaced from the cannula 26 with the shell, in the embodiment illustrated in FIG. 1, encompassing the cannula 26 but being shorter at either end of the cannula 26. The cannula 26 includes an inlet and an outlet 30 and 32, respectively. Preferably, the inlet and the outlet 30 and 32 of the cannula 26 are blunt. Of course, if desired, either or both of these members could be pointed.

The shell 28 is intermediate of the cannula inlet and outlet 30 and 32. The cannula 26 and shell 28 define a second channel 34 therebetween. In a preferred embodiment, the periphery of the cannula 26 is circular along its length. Similarly, the internal surface of the shell 28 is preferably arcuate and preferably circular along its length.

The second channel 34 includes a channel inlet 36 defined between the shell 28 and the cannula 26, short of the cannula 34 outlet 32. Similarly, the second channel includes a channel outlet 38 defined by the shell 28 and the cannula 26, short of the cannula inlet 30.

The cannula 26 is secured to the shell 28 whale still maintaining an open flow path through the channel inlet 36, the channel 34, and the channel outlet 38. Thus, a very small flow path is created outside a single cannula with precision.

The upper section 16 of the cartridge 12 is designed to preferably receive a diluent. To this end, in the preferred embodiment illustrated, the upper section 16 includes a first and second section 40 and 42, respectively. As illustrated in FIG. 2, the first section 40 is designed to house the diluent 43.

In order to prevent the diluent from flowing from the first section 40 out through the channels 27 and 34, as illustrated in FIG. 1 a sheath 44 is provided for covering the end of the cannula 26 and shell 28. Preferably, the sheath 44 is substantially similar to that disclosed in U.S. Pat. No. 5,167,642 entitled: "SHEATH FOR CANNULA", the disclosure of which is incorporated herein by reference. As set forth in that patent application, the sheath 44 provides a water tight seal thereby preventing any of the diluent from leaking out of either of the channels defined by the cannula 26 or shell 28.

However, the sheath 44 is also so constructed and arranged that even when used with a blunt ended cannula 26, the sheath will rip, not core, upon the exertion a sufficient force by the blunt end of the cannula against the walls 46. This allows the blunt end of the cannula 26 to be received within an injection site without first having,to manually remove the sheath 44. The sheath 44 will fold back along the cannula 26 and shell 28 in an accordion fashion. This will allow the blunt end of the cannula 26 and shell 28 to enter the injection site, but prevent the sheath 44 from entering the injection site.

Due to the use of the sheath, the entire first section 40 of the adaptor 12 can be filled with diluent if desired. Additionally, if desired, a removable cover 47 can be provided to protect the sheath 44 prior to use of the cartridge.

To divide the upper section 16 into first and second sections 40 and 42, a wall 48 is provided. Preferably, the wall 48 includes means for piercing a vial. In the preferred embodiment illustrated, the wall 48 includes a spike 50 that provides fluid communication between the first and second sections 40 and 42. The wall 48 prevents diluent housed in the adaptor 10 from leaking out of a top of the first section 40 of the adaptor 10.

The spike 50 provides means for providing fluid communication between the first section 40 of the adaptor 10 and a vial 54 to be docketed on the second section 42 of the adaptor 10. Of course, any piercing means that allows fluid flow between the vial 54 and the adaptor 10 can be used. As illustrated, preferably, the spike 50 includes a foil seal 56 to prevent leakage of the diluent prior to docking with a vial 54. Additionally, to insure the sterility of the spike 50, a removable cover 58 can be provided.

In the preferred embodiment illustrated, the spike 50 is located so as to be recessed from a plane defined by an open end of the second section 42. Because the spike 50 is recessed, this acts to reduce accidental "sticks" of personnel handling the adaptor 10 as well as prevent touch contamination.

If desired, the second section 42 can include on an interior surface bumps (not shown) having a sloped side facing the open end of the second section. Such a structure assists in securing a vial 54 to the adaptor 10. An example of such a structure is set forth in PCT Published Application No. WO91/11152, the disclosure of which is hereby incorporated herein by reference.

As illustrated in FIG. 2, in use, a vial 54 is mated with the adaptor 10. To this end, at least the top portion 56 of the vial 54 is received in the second section 42 of the adaptor 10. This causes the spike 50 to pierce a rubber stopper 58 of the vial 54, establishing fluid communication between the cartridge 12 and the vial 54. Due to the construction of the cartridge 12, the cartridge can mate with any standard off-the-shelf vial 54 containing a beneficial agent.

Pursuant to the present invention, at least a portion of the walls 60 that define the first section 40 can be biased inwardly, as illustrated in phantom lines in FIG. 1. Preferably, at least a portion of the walls 60 are constructed from a flexible material. The material, however, should be sufficiently rigid to provide stability to the adaptor 10, but allow the walls 60 to be biased inward. In a preferred embodiment, the entire walls 60 are flexible. Conversely, the walls 61 that define the second section 42, if desired, can be rigid.

As illustrated in FIG. 3, in order to reconstitute or dilute a drug 65 contained in the vial 54, the adaptor 10 is turned upside down. Diluent 43 contained in the adaptor 10 is then forced into the vial 54 by squeezing the flexible walls 60 of the adaptor. This forces the diluent 62 from the adaptor 10 into the interior of the mated drug vial 54.

The drug 65 contained within the vial 54 is then allowed to dissolve and/or mix with the diluent. The resultant drug solution is then transferred back into the adaptor 10 by holding the adaptor 10 in an upright position such that the solution is at the stopper end of the vial 54. The adaptor 10 is then compressed forcing air into the vial 54. The higher pressure in the vial 54 then forces the liquid from the vial into the adaptor 10.

Figures 4, 5, 6, 7, 8, 9:
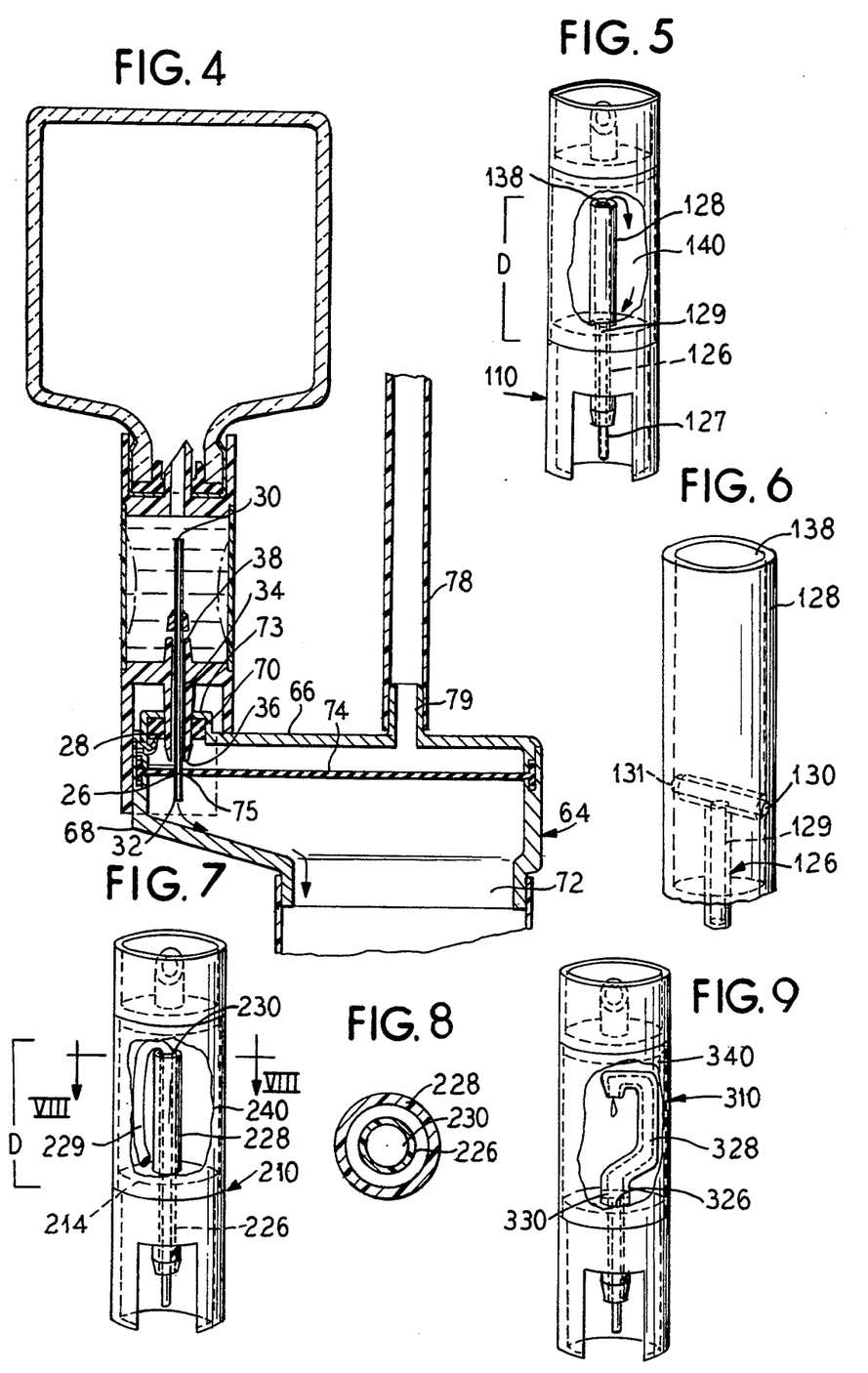
FIG. 4 illustrates the vial and adapter arrangement of FIG. 2 mated to an infusion set.
FIG. 5 illustrates an embodiment of the adaptor of the present invention.
FIG. 6 illustrates an enlarged perspective view of the flow paths of the embodiment of FIG. 5 with parts broken away.
FIG. 7 illustrates a further embodiment of the adaptor of the present invention.
FIG. 8 illustrates a cross-sectional view of the cannula of the adaptor of FIG. 7 taken along lines VIII—VIII.
FIG. 9 illustrates still a further embodiment of the adaptor of the present invention.

Referring now to FIG. 4, the adaptor 10 can then connected to an IV administration set, for example, the Mainstream TM administration set available from Baxter Healthcare of Deerfield, Illinois. The drug that was contained in the vial 54 can now be delivered to the patient. To accomplish this, the adaptor 10 is docketed on a receptacle 64. The receptacle 64 includes upper and lower fitments 66 and 68. The upper fitment 66 includes an inlet 70. The lower fitment 68 includes the outlet 72. A pierceable resealable injection site 73 is mounted within the upper fitment 66 of the receptacle 64. An example of such an IV administration set is disclosed in U.S. Pat. No. 4,804,366, the disclosure of which is incorporated herein by reference.

The receptacle 64 includes a resilient divider 74 trapped between the upper and lower fitments 66 and 68 of the receptacle 64. The resilient divider 74 defines a narrow through bore 75 directly below the resilient pierceable injection site 70. Before the cartridge 10 of the present invention is engaged with the receptacle 64, fluid flowing from a parenteral container 76 flows through the fluid conduit 78 and through a receptacle inlet 79 whereon it flows into the receptacle 64 above the dividing plate 74, through the through bore 75 and downstream to the receptacle outlet 72. Fluid then flows downstream to the patient.

As illustrated in FIG. 4, when the cartridge 12 is mounted on the receptacle 64, the cannula 26 and the shell 28 pierce the resilient injection site 70. The cartridge 12 continues to be urged downwardly so that the cannula outlet 30 enters the through bore 75 and is liquid-sealingly engaged by the resilient divider 74 around the periphery of the cannula outlet 32.

Upon engagement of the cartridge 10 and receptacle 64, as illustrated in FIG. 4, liquid flowing into the receptacle 64 at the inlet 79 is prevented from passing through the through bore 75 and the receptacle 64 because the resilient divider 74 has been sealed about the cannula outlet 32 portion at the through bore 75. Thus, liquid entering the receptacle 64 enters the channel inlet 36, flows through the channel 34, and enters the first section 40 at the channel outlet 38.

In an embodiment, as liquid rises within the first section 40, it will continue to rise until it reaches the cannula inlet 30, whereupon liquid begins to exit the chamber through the cannula 26 downstream through the cannula outlet 32. Liquid exiting the cannula 26 has an appropriate concentration for the beneficial agent mixed therewith for delivery to the patient. In the illustrated embodiment, the upward liquid flow path created within the first section 40 by the shell 28, channel 34, and cannula 26 creates a density gradient within the first section 40 such that the concentration of drug within the liquid exiting at the cannula outlet 32 will not be so high as to create local toxicity of the patient.

As illustrated in the FIGS., many embodiments of the adaptor 12 are possible. The drug delivery to the patient must meet clinical guidelines. For IV therapy, these guidelines may include parameters such as delivery rate, delivery volume, and delivery concentration. Typically, the clinical guidelines for drug delivery specify a range in which the drug delivery parameters should lie. Drug delivery rates, concentrations, and volumes can be controlled by modification of the adaptor 10.

The geometry of the adaptor 10, diluent flow path, drug solution density, and drug solution volume all can be tailored to yield a desired drug delivery profile for a particular drug. Adaptor 10 design modifications can yield drug delivery rates which range from bolus IV injection to IV drip infusion.

The density of the drug solution relative to that of the diluent has a major impact on the rate of drug delivery from the adaptor 10. For a given adaptor design, the relative density of the diluent and drug solution determine the mixing characteristics in the adaptor 10 during delivery to the administration set. The adaptor 10 may be designed so that by varying only the relative density of the drug solution and diluent, the delivery rate from the adaptor can range from bolus IV to injection to IV drip infusion.

Drug delivery rates, volumes (volume required to deliver the dose), and concentrations are functions of the volume of solution in the adaptor 10. Therefore, by controlling the solution volume in the adaptor 10 drug delivery to the patient can be governed.

The drug delivery rate, volume, and maximum effluent concentration from a "well stirred vessel" can be expressed as:

Delivery rate: $dD/dt = D\ F/V$
Delivery volume: $L = -V\ \ln(D/D_o)$
Maximum effluent concentration: $M = D_o/V$
D: amount of drug in the adaptor $D_o$: initial amount of drug in the adaptor
t: time
F: diluent flow rate
V: volume of solution in the adaptor The drug delivery rate, volume, and maximum effluent concentration from a vessel exhibiting plug flow can be expressed as:

Delivery rate: $dD/dt = F\,D_0/V$
Delivery volume: $L = V\,(D_o - D)/D_o$
Maximum effluent concentration: $M = D_0/V$
D: amount of drug in the adaptor
$D_o$: initial amount of drug in the adaptor
t: time
F: diluent flow rate
V: volume of solution in the adaptor The above expressions for rate of delivery from the two vessel types show that the delivery rate is directly proportional to the flow rate and inversely proportional to the volume of solution in the vessel. Therefore, as the mixing in the adaptor 10 approaches either of the two ideal systems described, by adjusting the volume of the solution in the adaptor, the delivery rate to the administration set can be governed.

The above expressions also indicate that the delivery volume is directly proportional to the volume of solution in the adaptor 10; and the maximum effluent concentration is inversely proportional to the solution volume in the adaptor. Therefore, as the mixing in the adaptor 10 approaches either of the two ideal systems described, both parameters for a given drug can be controlled by adjusting the solution volume in the adaptor.

The internal geometry of the adaptor 10 can be designed to effect mixing of the diluent and drug solution in the adaptor 10 which will consequently affect the rate of drug delivery from the adaptor 10 to the administration set. The fluid path of the adaptor 10 can be designed to affect the mixing and consequently the delivery kinetics from the adaptor. By changing the positions of the fluid inlet and outlet, the mixing of the adaptor 10 for a given drug solution can range from approximately plug flow to approximating a well-stirred vessel.

Referring now to FIGS. 5 and 6, an embodiment of the fluid path within the adaptor is illustrated. In the illustrated embodiment, the fluid path of the adaptor 10 illustrated in FIGS. 1 and 4 is modified. To this end, the fluid flow paths in the lower section 118 of the embodiment of FIGS. 5 and 6 are substantially similar to that of the sleeve and cannula illustrated in FIGS. 1–4. However, the fluid flow paths of the fluid outlet within the first section 140 are modified.

To this end, in the embodiment of the adaptor 110 illustrated in FIG. 5, instead of a cannula structure that extends into the first section 140, a T-shaped fluid flow path 126 is provided. The fluid flow path 126 includes a lower cannula structure 127 but includes an upper T-shaped structure 129. Fluid flow out of the first section 140, as illustrated in FIGS. 5 and 6, is through two openings 130 and 131 of the T-shaped structure 126.

Instead of the shell structure 28 of FIGS. 1–4, fluid flows into the first section 140 through an extended flow path 128. The extended flow path includes an outlet 138 located near a top of the first section 140. This creates a fluid flow within the first section 140 illustrated in FIG. 5.

Accordingly, the fluid inlet, with respect to the first section, is distal and the fluid outlet is proximal relative to the docking site. The distance D can be modified to yield optimal drug delivery parameters for a given drug.

FIGS. 7 and 8 illustrate another embodiment of the adaptor 210. In this embodiment, the cannula 226 and shell 228 extend for substantially the same distance into the first section 240. However, a tube 229 is connected to the inlet 230 of the cannula 226 allowing the fluid outlet path to be modified within the first section 240.

In the illustrated embodiment, the tube 229 and thereby fluid outlet path is positioned near the wall 214 at a bottom of the first section 240. In this version, again, the fluid inlet, into the first section 240, is distal and the fluid outlet is proximal relative to the docking site. The distance D can be modified to yield optimal drug delivery parameters for a given drug.

FIG. 9 illustrates a further embodiment of the adaptor 310 present invention. In this embodiment, again, the fluid outlet path 326 is defined by a T-shaped member. The fluid inlet path is defined by an extended member 328 that extends near a top of the first section 340.

The fluid inlet 338 is therefore distal and the outlet 330 proximal to the docking site. The inlet 338 is positioned above the solution levels. The fluid inlet 338 is constructed so that it creates droplets of fluid accordingly, as diluent enters the adaptor 310, it drops into the solution. The drops of diluent falling into the adaptor solution will increase the mixing in the adaptor 310. The location of the fluid outlet can be modified so as to optimize drug delivery for a given drug.

In an embodiment, it is possible for the adaptor 10 to be designed to contain drug in a liquid state within the first section 40. The drug formulation can thereby be stored in the adaptor body. A site for vial 54 access therefore would not be necessary.

If desired, the fluid, drug or diluent, can be a frozen solution stored in the adaptor 10. The solution then being thawed and the adaptor 10 docketed to the Mainstream TM access site.

Figure 10:
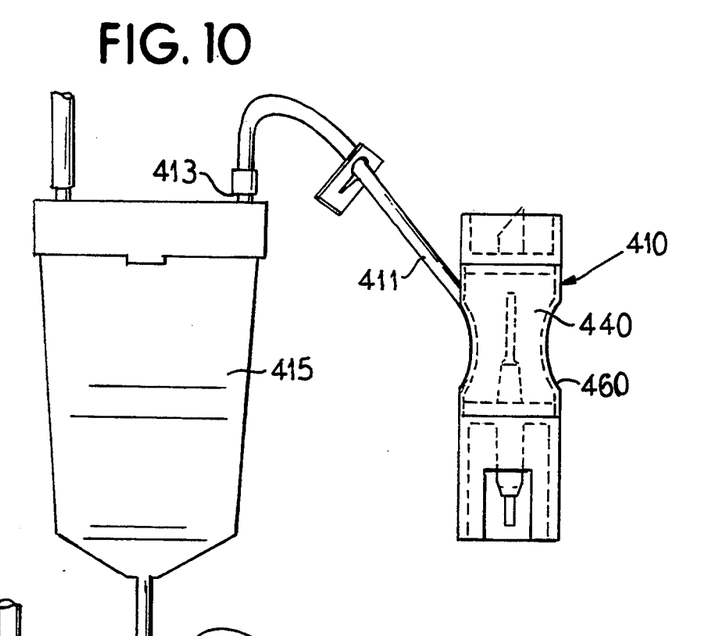
FIGS. 10-12 illustrate perspective views of an embodiment of the present invention illustrating a method for filling the adaptor with a diluent.
Figures 11, 12:
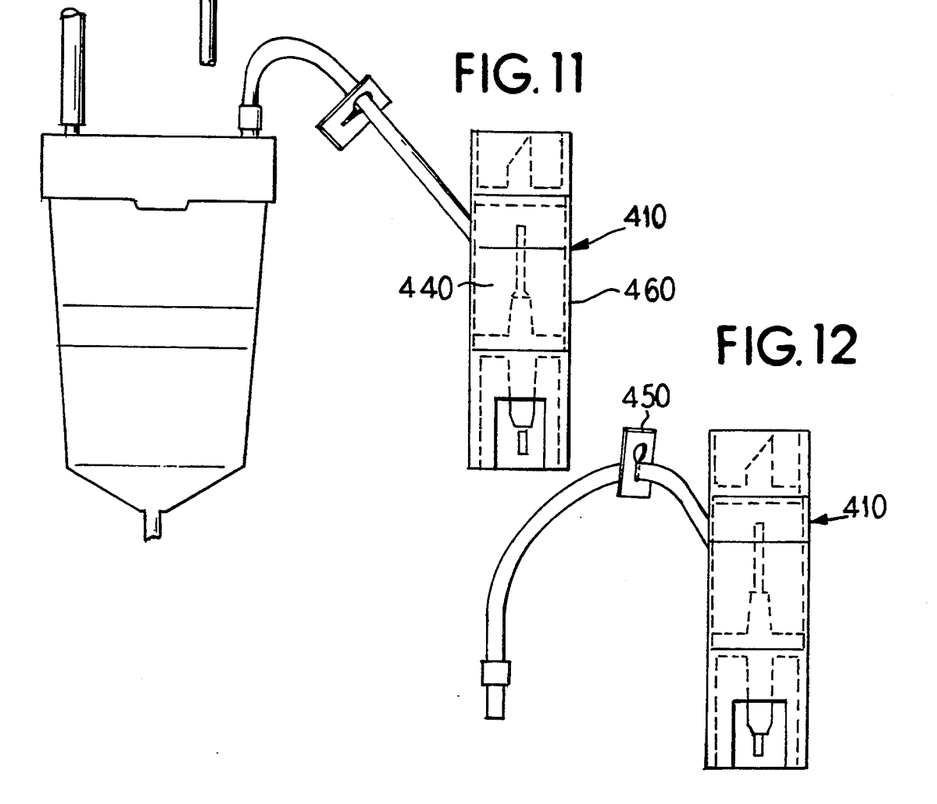

Although the adaptor 10 in a preferred embodiment, is provided to the end user containing diluent, the adaptor may be provided to the end user without diluent. As illustrated in FIGS. 10–12, a method for filling the adaptor 410 with diluent is illustrated.

In the illustrated embodiment, the adaptor 410 includes a conduit 411 that is in fluid communication with the first section 440. The operator plugs the conduit 411 from the adaptor 410 into an access site 413 of an IV container 415. This can be the IV container that is used to administer the drug to the patient in the IV administration set. The operator then squeezes the flexible chamber 460 of the adaptor body 410 expelling air into the IV container 415, as illustrated in FIG. 10.

Referring now to FIG. 11, by releasing the walls 460 of the adaptor 410, diluent 421 will be drawn into the adaptor 410. As illustrated in FIG. 12, after the desired amount of diluent is transferred into the adaptor 410, the conduit 411 would be clamped off, using a clamp 450 or other means, and the adaptor used as described above.

Of course, a variety of other means can be used for filling the adaptor.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A device for coupling a first container including a beneficial agent to a second member, the device comprising:
   a substantially hollow member;
   a fluid path, having a channel including a first opening and a second opening, mounted within a wall that divides the substantially hollow member into an upper section and a lower section, the upper section including means for receiving at least a portion of a first container and the substantially hollow member including walls that define an exterior of the upper section that are capable of, at least in part, being biased inwardly; and
   a fluid within the upper section wherein the walls of the upper section exert pressure on the fluid.

2. The device of claim 1 wherein the substantially hollow member includes walls that define the lower section that are substantially rigid.

3. The device of claim 1 wherein the substantially hollow member has a tube-like shape.

4. The device of claim 1 further comprising a shell circumscribing a portion of the fluid path and defining a second channel having a first opening and a second opening.

5. The device of claim 4 wherein the first opening of the fluid path and the first opening of the shell extend into the upper section at substantially the same level.

6. The device of claim 4 wherein the first opening of the fluid path extends into the upper section a greater distance from the wall than the first opening of the shell.

7. The device of claim 1 wherein the substantially hollow member includes means for piercing a closure of the first container when the first container is received by the upper section.

8. The device of claim 1 wherein the fluid path is a cannula.

9. The device of claim 8 wherein the cannula includes at least one blunt end.

10. The device of claim 1 wherein the fluid path terminates in a structure having a T-like cross-sectional shape.

11. The device of claim 1 wherein the walls are substantially flexible.

12. The device of claim 1 wherein the upper section includes a conduit, coupled to the walls, for allowing the upper section to receive fluid.

13. The device of claim 1 wherein the upper section includes an upper wall located at a distance from the wall dividing the hollow member, the upper wall includes a spike and defines an upper area for receiving a portion of a vial.

14. The device of claim 1 wherein the upper section includes a liquid.

15. A cartridge for introducing a beneficial agent into a fluid conduit for delivery of the beneficial agent comprising:
   a hollow tube having a wall member dividing the hollow tube into upper section and a lower section;
   a cannula mounted within the hollow tube defining a channel having an inlet and an outlet;
   a shell circumscribing a portion of the cannula and defining a channel having an inlet and an outlet wherein the channels of the cannula and the shell pass through the wall; and
   the upper section being so constructed and arranged to receive at least a portion of a vial including a beneficial agent, the upper section being defined, at least in part, by substantially flexible walls.

16. The cartridge of claim 15 wherein the substantially hollow member includes walls that define the lower section that are substantially rigid.

17. The cartridge of claim 15 wherein the substantially hollow member includes means for piercing a closure of the vial when the vial is received by the upper section.

18. The cartridge of claim 15 wherein the cannula includes at least one blunt end.

19. The cartridge of claim 15 further comprising a sheath for covering at least an end of the cannula and the shell that extends into the lower section.

20. The cartridge of claim 19 wherein the sheath includes a body member defining an interior for receiving at least a portion of the end of the cannula, the body member including a first end and a second end, the second end having an opening for receiving at least a portion of the cannula, the first end including a wall member so constructed and arranged as to rip upon the exertion of a sufficient perpendicular force by the end of the cannula, and the body includes side walls extending between the first end and the second end, the side walls are so constructed and arranged so as to slide back along the cannula toward the second end upon the tearing of the first end by the cannula and the application of a sufficient force upon the side walls.

21. The cartridge of claim 15 wherein an opening of the cannula and an opening of the shell terminates at approximately the same position in the upper section.

22. The cartridge of claim 15 wherein an opening of the cannula that extends into the upper section is coupled to a fluid tube having an outlet.

23. The cartridge of claim 22 wherein the outlet of the fluid tube is located in juxtaposition to the wall.

24. The cartridge of claim 15 including a fluid conduit in fluid communication with the upper section for providing fluid flow into the upper section from a fluid source.

25. The cartridge of claim 15 wherein the upper section includes a liquid.

26. The cartridge of claim 15 wherein the upper section includes a frozen beneficial agent.

27. The cartridge of claim 15 wherein the upper section is divided into a first section for receiving a fluid and a second section for receiving the portion of the vial, and the upper section includes a spike that provides fluid communication between the first section and the second section.

28. The cartridge of claim 27 further comprising a closure for covering at least a portion of the spike prior to use of the cartridge.

29. A drug delivery device comprising:
   a cartridge body including an upper section defining a vial receiving area having a rigid base wall and means for puncturing a top of a vial so received, the cartridge body including two channels through a wall member that divides the cartridge body into the upper section and a lower section, the upper section being defined, in part, by substantially flexible walls; and
   a vial including a beneficial agent attachable to the cartridge body at the upper section defining the vial receiving area.

30. The device of claim 29 wherein the cartridge body includes walls that define the lower section that are substantially rigid.

31. The device of claim 29 wherein one of the two channels terminates in a structure having a T-like cross-sectional shape.

32. The device of claim 29 wherein a first opening of each of the channels extends into the upper section at substantially the same level.

33. The device of claim 29 wherein a first opening of each of the channels extends into the upper section at a different location.

34. The device of claim 29 further comprising a sheath for covering at least an end of each of the channels that extend into the lower section.

35. The device of claim 29 wherein the upper section includes a liquid.

36. The device of claim 29 wherein the upper section includes a frozen liquid.

37. The device of claim 29 wherein the vial receiving area of the upper section includes rigid walls.

38. The device of claim 29 wherein the means for puncturing the top of the vial is a spike.

39. A method for drug delivery comprising the steps of:
providing an adaptor having an upper section and a lower section divided by a wall and two flow paths between the upper section and the lower section;
locating a liquid in the upper section of the adaptor;
coupling a vial containing a beneficial agent to the upper section of the adaptor;
establishing fluid communication between the upper section and an interior of the vial;
biasing a portion of a wall defining the upper section toward an interior of the upper section to cause the liquid to flow into the vial;
allowing a resultant liquid in the interior of the vial to flow into the upper section; and
coupling the adaptor to a device for delivering the resultant liquid to a patient.

40. The method of claim 39 wherein the vial is coupled to the adaptor before fluid is housed in the upper section.

41. The method of claim 39 further comprising the step of removing a cover from the upper section prior to coupling the vial to the adaptor.

42. The method of claim 39 further comprising the steps of: providing a sheath for covering an end of the flow paths that extend into the lower section; and causing the sheath to be removed from the openings of the flow paths as the adaptor is coupled to the device.

43. The method of claim 42 further comprising the step of causing the sheath to rip as the adaptor is coupled to the device.

44. The method of claim 39 wherein the device is an IV administration device.

45. The method of claim 39 further comprising the steps of causing a fluid to flow into the adaptor, and allowing the fluid to mix with the resultant liquid to create an administratable fluid for delivery to a patient.

46. The method of claim 39 further comprising the step of delivering the administratable fluid to a patient.

47. The method of claim 39 further comprising the step of providing the upper section with means for piercing, automatically, a portion of the vial as it is coupled to the upper section.

* * * * *